(12) United States Patent  (10) Patent No.: US 8,914,104 B2
Kubat et al.  (45) Date of Patent: Dec. 16, 2014

(54) DUAL-MODE DEFIBRILLATOR WITH LATCHED PANEL (75) Inventors: John Kubat, Townsend, MA (US);
Fredrick Faller, Burlington, MA (US);
Ziad F. Elghazzawi, Newton, MA (US);
Peter A. Lund, Nashua, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 445 days.

(21) Appl. No.: 12/956,906

(22) Filed: Nov. 30, 2010

(65) Prior Publication Data

US 2011/0130799 A1  Jun. 2, 2011

Related U.S. Application Data (60) Provisional application No. 61/265,299, filed on Nov. 30, 2009.

(51) Int. Cl.
*A61N 1/08* (2006.01)
*E05C 19/16* (2006.01)
*E05B 17/00* (2006.01)
*E05B 1/00* (2006.01)
*E05B 65/00* (2006.01)
*A61N 1/39* (2006.01)

(52) U.S. Cl.
CPC ............ *A61N 1/3968* (2013.01); *E05B 1/0007* (2013.01); *E05B 65/006* (2013.01); *E05C 19/16* (2013.01); *A61N 1/3993* (2013.01); *E05B 17/0033* (2013.01)
USPC .......................................................... 607/5

(58) Field of Classification Search
USPC ............................................................ 607/5
See application file for complete search history.

(56) References Cited

U.S. PATENT DOCUMENTS 3,744,833 A    7/1973  Berducone
5,076,623 A    12/1991 Richards
(Continued)

FOREIGN PATENT DOCUMENTS

JP    01-244694    9/1989
JP    01-174978    12/1989
JP    2004-512909    4/2004

OTHER PUBLICATIONS

International Preliminary Report on Patentability for Application No. PCT/US2010/058410, dated Jun. 14, 2012, 10 pages.

(Continued)

*Primary Examiner* — Luther Behringer
(74) *Attorney, Agent, or Firm* — Fish & Richardson P.C.

(57) ABSTRACT

A medical device includes a device housing and a door mounted to the device housing. The device also includes a first magnet mounted to the door, wherein magnetic force applied to the door exerts a moment on the door, and a second magnet mounted in the housing and positioned to hold the door shut by magnetic interaction with the first magnet. In addition, the device includes a user-movable mode-changing mechanism attached to a third magnet, and arranged to hold the third magnet out of proximity with the first and second magnets when the device is in a first mode, and to move the third magnet into proximity with the first and second magnets when the device is in a second mode so as to expel the first magnet away from the housing and open the door to expose items positioned behind the door.

13 Claims, 6 Drawing Sheets

(56) References Cited

U.S. PATENT DOCUMENTS

| | | | |
|---|---|---|---|
| 6,021,349 A | | 2/2000 | Arand et al. |
| 2002/0072774 A1 | | 6/2002 | Daynes et al. |
| 2003/0208237 A1 | * | 11/2003 | Locke et al. ................ 607/5 |
| 2006/0049645 A1 | | 3/2006 | Drumm |
| 2007/0038256 A1 | * | 2/2007 | Maschke ..................... 607/6 |
| 2007/0039141 A1 | | 2/2007 | Rairden |
| 2007/0056603 A1 | | 3/2007 | Huh |

OTHER PUBLICATIONS

International Search Report & Written Opinion for Application No. PCT/US2010/058410, dated Jan. 26, 2011, 11 pages.

Japanese Office Action, with English translation, JP Application No. 2012-541228, mailed Aug. 19, 2014, 6 pages.

* cited by examiner

DUAL-MODE DEFIBRILLATOR WITH LATCHED PANEL

CROSS-REFERENCE TO RELATED APPLICATIONS

This application claims priority to U.S. Provisional Patent Application Ser. No. 61/265,299 to John Kubat et al., entitled "Dual-Mode Defibrillator With Latched Panel," and filed Nov. 30, 2009, the contents of which are incorporated herein by reference.

TECHNICAL FIELD

This document relates to automatically exposing physical components on a medical device such as a defibrillator.

BACKGROUND

Sudden cardiac arrest (colloquially "a heart attack") is a serious condition that frequently results in death. The speed with which life saving personnel can respond to a sudden cardiac arrest is one of the most important, if not the most important, determinant of a successful outcome for a victim of sudden cardiac arrest. For example, it is said that likelihood of surviving a sudden cardiac arrest falls ten percent for every minute in which assistance (e.g., defibrillation or chest compressions) is delayed. As a result, speed of response can be very important to a heart attack victim.

One typical mode of treatment for sudden cardiac arrest is to "shock" the heart back into a steady beating pattern using an external defibrillator. Such a defibrillator commonly includes a pair of electrodes that are placed on the victim's chest and are connected electrically to a power unit. In hospitals, such a defibrillator is typically used by a "code team" that responds to "codes" issued by attending caregivers. Such teams use advanced defibrillators that they can control for a number of parameters, such as by displaying a patient's ECG and blood oxygen level, and by letting caregivers set the power level to be delivered to the victim and provide pacing inputs.

Such professional defibrillators, known as Advanced Life Support, or ALS, defibrillators, can be intimidating for other staff, including medically-trained staff such as shift nurses. As a result, a patient may have to wait for a code team to arrive even though an otherwise-competent caregiver is nearby.

SUMMARY

This document describes systems and techniques that may be used to provide a dual-mode external defibrillator. In one mode, the defibrillator may be used as an ALS defibrillator, and in another mode, it may be used as a Basic Life Support, or BLS, defibrillator. The different modes present substantially different "looks" to a user, where the BLS mode provides a simplified device or interface, as compared to the ALS mode.

Certain indicators that are lit by the defibrillator and are visible from the front of the defibrillator may be concealed during BLS mode so that a caregiver with a lower level of training will not be distracted or intimidated by such indicators. The indicators may include, for example, lights that indicate whether the defibrillator is currently analyzing a patient's readings and/or is charging a defibrillator circuit. The indicators may also be integrated with buttons on the device, so that the user can see that the buttons are available for selection when the device is in ALS mode, but not see the buttons at all (and the buttons are not available for selection) when in BLS mode. Such selective display of the indicators can be provided using a specially printed label between the front surface of the defibrillator and light sources that backlight the label. Specifically, text or graphics can be "dead fronted" by placing a layer having a comparatively dark translucent ink on it in line with the text or graphics on another layer. In this manner, the text or graphics is hidden from being seen from the front of the device until substantial light is provided from behind the text and graphics, from inside the defibrillator housing. LEDs placed inside the housing may be connected so as to be energized when the defibrillator is in ALS mode, so that the enhanced ALS capabilities of the device can be announced simultaneously to a user.

Certain components are best implemented in a manner other than a lighted button, however. For example, certain parameters of a defibrillator are best adjusted in a continuous manner, so that a rotating knob or dial is a preferred interface for a user of the device. The power delivered for pacing with a device may be such a parameter, for example. One way to prevent such physical mechanisms from being visible in a mode such as a BLS mode, is to place a door, or panel, in front of the mechanisms, where a user can manually pull the door open when the mechanisms are needed. But a user may not notice that the adjustments are available to them, or they may not want to take the time to locate the knobs and deal with them.

Thus, as described below, mechanisms can provide for the automatic revealing, from behind a cover, of user-adjustable controls on a defibrillator when the defibrillator is switched from basic mode to advanced mode. The cover may be "kicked" out into an open position by connecting a magnet to a knob whose rotation switches the defibrillator from one mode to another. That magnet, alone or in combination with another magnet held in the defibrillator housing in close proximity to a corresponding magnet in the door, may cause the door to be held closed when the knob is in a first positions, and kicked open when the knob is in a second position.

Implementations of these features may provide for one or more advantages. For example, BLS capabilities may be provided conveniently in a hospital setting so that immediate on-site caregivers can provide immediate defibrillation to a patient who suffers a sudden cardiac arrest. The further capabilities of an ALS mode, including physical adjustment mechanisms, may be hidden in BLS mode so that such a caregiver may readily provide therapy to a patient, and not be distracted by options that are not of interest to them. Also, a single defibrillator may be used for both BLS and ALS purposes. As a result, a hospital need not buy or store as many defibrillators, and a ward will be less cluttered with equipment, so that the defibrillator can be kept closer to a patient as a result (though the hospital may purchase more defibrillators in the end, if they become particular useful). Also, the defibrillator may provide both BLS and ALS functionality, and may switch between the two modes essentially seamlessly. For example, a shift nurse could start a defibrillator in BLS mode and provide immediate care to a patient suffering from sudden cardiac arrest, and when the code team arrives, it could switch the unit to ALS mode for more detailed treatment of the patient. Such a switchover can be achieved without having to remove and replace electrodes that the initial caregiver applied, so that the patient can receive basic care very quickly and can shift to more advanced care quickly also. As a result, the patient's chance of survival may be maximized.

Also, use of enclosed magnets for latching and unlatching of a cover may have additional benefits in certain implementations. For example, the magnets may permit latching and unlatching without the need for physical mechanisms or corresponding that mate with each other to latch, and that can be hard to clean as a result. Such mechanical mechanisms may also be prone to breaking, since an outward-extending hook is typically used to create a mechanical latch, and may thus be caught on other equipment, or on clothing, causing the hook to snap off. Also, the use of magnetic unlatching mechanisms may maintain a door in an open position as long as a device is in a particular mode, so that a user will not accidentally cover up functionality that is available with the current device mode.

In one implementation, a multi-mode electronic medical device is disclosed which comprises a device housing, and a door mounted to a front side of the device housing at a hinge along a first edge of the door, wherein the door has an open position and a closed position. The device also includes a first magnet mounted to the door away from the first edge of the door, wherein magnetic force applied to the door exerts a moment on the door about the hinge, a second magnet mounted in the housing and positioned to hold the door shut by magnetic interaction with the first magnet, and a user-movable mode-changing mechanism attached to a third magnet. The mechanism is arranged to place a third magnet out of proximity with the first and second magnets when the device is in a first mode, and to move the third magnet into proximity with the first and second magnets when the device is in a second mode so as to expel the first magnet away from the housing and open the door to expose items positioned behind the door.

The user-movable mode-changing apparatus can comprise a rotary switch, and the third magnet can be mounted in an off-center portion of the knob. Also, the second magnet can be positioned between the first and third magnets when the device is in a second mode so that the first magnet changes the polarity of the second magnet. The device can also comprise one or more user-manipulable devices located in an area that is hidden by the door when the device is in the first mode. In addition, the device can include a plurality of visual indicators that are hidden from a user of the device when the device is in the first mode, and are back-lit to be visible by the user when the device is in the second mode. In some aspects, the second magnet comprises a spherical magnet that is mounted so as to be free to rotate in the device.

In another implementation, a multi-mode electronic medical device is disclosed that comprises a device housing, and a panel mounted to a front side of the device housing, wherein the panel has an open position and a closed position. The device also includes a first magnet mounted to the panel, a second magnet mounted to a user-movable mechanism on the device whose movement from a first position to a second position changes the device from a first mode to a second mode and also moves a second magnet relative to the first magnet so as to automatically move the panel from a closed position to an open position when the device changes from the first mode to the second mode. The first mode can be an advanced life support mode and the first mode is a basic life support mode for a defibrillator. Also, the panel can include a hinge along a first edge, and the first magnet can be mounted to the panel along a second edge that is opposite the first edge. The device can also include a third magnet positioned to be located between the first magnet and the second magnet when the device is in the second mode.

In some aspects, the third magnet is a rotatable spherical magnet that is arranged to change polarity when the second magnet is brought in close proximity to the third magnet. In addition, the user-movable mechanism can comprise a rotatable user-manipulable knob, and the second magnet is mounted in an edge of the knob. The device can also comprise a plurality of visual indicators that are hidden from a user of the device when the device is in the first mode, and are back-lit to be visible by the user when the device is in the second mode. In addition, the device can include an electronic display connected to a processor programmed to display a first set of instructions when the device is in the first mode, and a different, second set of instructions when the device is in the second mode. The processor can be programmed to provide audible instructions to a user of the device in coordination with instructions provided on the electronic display.

In yet another implementation, a multi-mode electronic medical device comprises a device housing, a movable door mounted to the device housing, wherein the door has an open position and a closed position, a first magnet mounted to the door, and means for moving the door from the first position to the second position when the device is switched form the first mode to the second mode, by magnetic cooperation with the first magnet.

In another implementation, a method of operating a multi-mode medical device is disclosed. The method comprises powering up the device, moving a control on the device from a first position that corresponds to a first operating mode for the device, to a second position that corresponds to a second operating mode for the device, causing a first magnet attached to the control to move from a first position to a second position, creating magnetic interaction with the first magnet to cause a second magnet that is mounted to a door on the device to cause the door to move from a first position to a second position, and electronically transitioning the device form the first mode to the second mode in coordination with causing the door to move from the first position to the second position. The first mode may be a basic life support mode for an external defibrillator, and the second mode may be an advanced life support mode for the external defibrillator. Also, moving the control can comprise rotating a knob on a face of the medical device. Moreover, creating magnetic interaction with the first magnet can comprise bringing the first magnet into proximity of a third magnet that had previously been holding the door in the first position.

The details of one or more embodiments are set forth in the accompanying drawings and the description below. Other features and advantages will be apparent from the description and drawings, and from the claims.

DETAILED DESCRIPTION

This document describes mechanisms by which a medical external defibrillator can provide interaction in both a BLS mode and an ALS mode. The techniques described here provide for convenient operation in BLS mode so that a relatively untrained user can operate the defibrillator. For example, features that may be desirable in an ALS mode can be hidden from a user in the BLS mode so that the user is not overwhelmed or confused. Certain such features may be manifested by physical objects that a user may manipulate to affect the operation of the defibrillator, and because they are physical, they must be concealed physically (e.g., by placing a cover over them) rather than electronically (e.g., by not displaying them on a screen).

As one example, human-manipulable physical devices, in the form of pacing adjustment knobs/dials, are normally hidden behind a door when a defibrillator is in BLS mode, so that basic caregivers need not be distracted by them. The defibrillator may also be provided with a human-movable device, in the form of a rotating knob, for converting the defibrillator to ALS mode (or more particularly, to a pacing mode within an ALS mode). The defibrillator may also be fitted with a plurality of magnets that cooperate, as the rotating knob is moved, to convert the door from a state in which it is held closed by magnetic attraction, to a state in which it is pushed open by magnetic opposition. Specifically, a magnet may be mounted in an edge of the door away from the door's hinge, and another magnet may be mounted in the housing for the defibrillator, so that the two magnets cooperate to keep the door closed in normal circumstances. A third magnet may be arranged to move in cooperation with the rotating knob so that it moves into the vicinity of the second magnet when the knob is rotated to change the defibrillator to ALS mode, thereby overpowering the second magnet and "kicking" the door open. The door will also not latch shut, in such a situation, until the defibrillator is switched back into BLS mode.

Figure 1A:
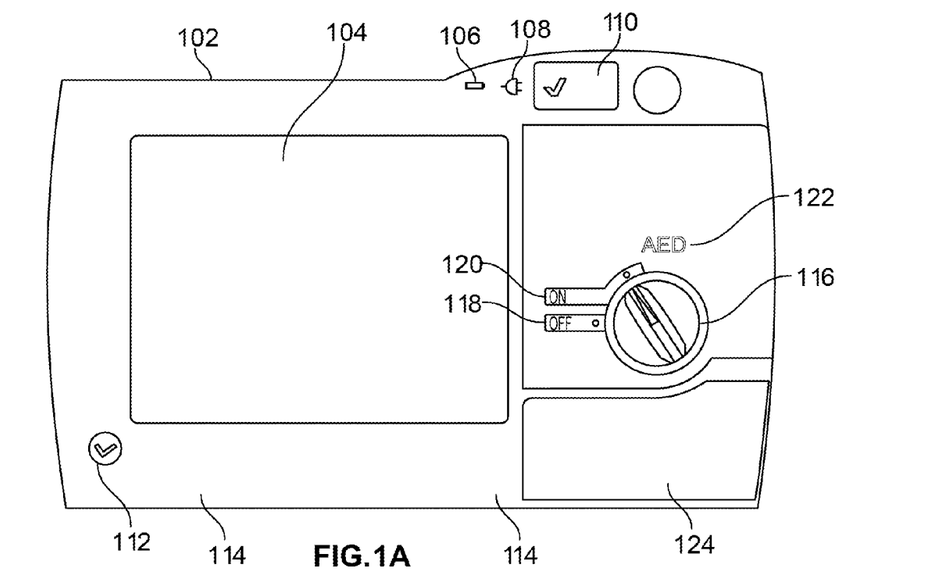
FIG. 1A shows a front of a dual-mode defibrillator in Basic Life Support mode.
Figure 1B:
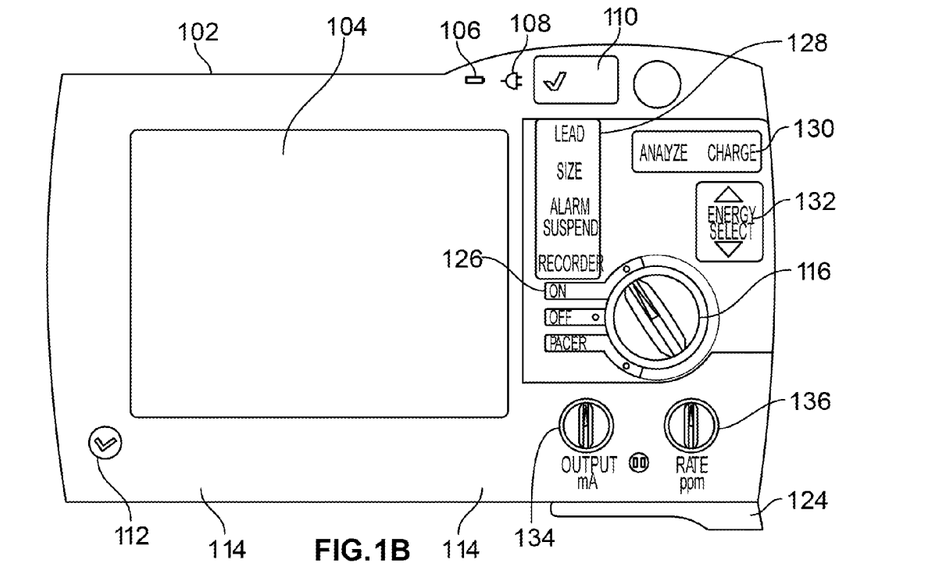
FIG. 1B shows a front of a dual-mode defibrillator in advanced life support mode.

FIG. 1A shows a front of a dual-mode defibrillator 102 in basic life support mode. FIG. 1B shows a front of the same dual-mode defibrillator 102 in advanced life support mode. Each figures shows the front surface of the defibrillator 102, with a number of features that can be seen by a caregiver when they are operating the defibrillator 102. The status or mode of the defibrillator 102 can be seen by a user, for example, from indicator 122 in FIG. 1A, where it is indicated that the device is on and is usable as an automated external defibrillator, or AED, which is a BLS mode. In FIG. 1B, many additional indicators and controls are shown, as the device has been changed to an ALS with Pacer mode by rotating knob 116 counterclockwise two spots to the "PACER" indication.

Referring now more specifically to items that are visible under both modes for the defibrillator 102, there is shown an electronic display 104, which may take the form of a cathode ray tube (CRT), liquid crystal display (LCD) panel, organic light emitting diode (OLED) panel, or other appropriate electronic display technology, that is preferably capable of providing both textual and graphical information to a user of the defibrillator 102 in a dynamic manner. In BLS mode, for example, the display 104 may be relatively unadorned, and may provide text to guide a user through the process of providing life support to a victim. For example, the display 104 may instruct the user textual or via simplified graphics to apply electrodes to the patient, to perform CPR, and to push harder or softer, or faster or slower, as the case may be, when they are providing chest compressions to the victim (as sensed, e.g., via an accelerometer that is provided in an assembly with the electrodes, and that the user push, within a housing, against the victim's chest when delivering chest compressions). Such instructions on the display 104 may also be accompanied by verbal instructions provided by a speaker in the defibrillator 102. The unit may enter BLS mode automatically when it is powered up, and then may be changed to ALS mode (and pacing mode) by an user.

In ALS mode, the display 104 may provide additional, and sometimes very detailed, information to the user. For example, the display may shown a ECG for the patient, a graph of CPR chest compressions over a past set period of time, the total elapsed time of performing CPR, the victim's pulse, and information about the electrode pads applied to the patent.

In addition, the lower edge of the display 104 may exhibit textual or graphical labels that correspond to a row of selection keys 114 (soft keys) that are arrayed below the display 104. Thus, for example, the row of labels may make up a menu of topics that a user may select by pressing an associated aligned key in order to see additional information about the defibrillator 102, or to change parameters for controlling the defibrillator 102.

Next to the selection keys 114 is an non-invasive blood pressure (NIBP) button 112. Selection of this button may allow the defibrillator 102 to measure a victim's blood pressure, which may in turn be shown on the display 104.

A number of additional indicators are displayed in both modes along the top of the defibrillator 102. For example, a battery indicator 106 may be made to light or blink to indicate to a user when battery reserve power is running low, so that the user may adjust their treatment of a victim accordingly or can seek out an AC power source for the defibrillator 102. Also, the battery level may be shown on an icon, such as by showing the image of the battery being "filled" to a degree that corresponds to the level of remaining battery power, a technique that is familiarly used on cellular telephones. In one implementation, a steady yellow indicator shows that the battery is charging, a steady green indicator shows that the battery is charged, and an alternating yellow and green indicator shows that no battery is installed or there is a battery charging fault.

In a similar manner, an AC power indicator 108 may be lit when the defibrillator 102 is plugged into an AC power source. The indicator may be visible, but not lit, when the defibrillator 102 is not plugged in, so that a user of the defibrillator 102 can know about the ability to plug the defibrillator 102 into a power source.

A code readiness indicator 110 is lit when the defibrillator 102 is ready for operation, based on a most recent self-diagnostic run. A green check mark indicates that the unit is ready for therapeutic use, while a red "X" indicates the defibrillator's 102 readiness is compromised and that it may not be ready for therapeutic use.

A mode selector knob 116 can be grasped by a user of the defibrillator 102 and rotated to select a mode in which to operate the defibrillator 102. The knob may typically be located in an "OFF" position (as indicated by an arrow indicator on a spine of the knob 116). In FIG. 1A, the knob has been turned clockwise by a user to point toward an "ON" position, in which the defibrillator 102 operates as an semi-automatic AED, as indicated by AED indicator 122.

As can be seen in FIG. 1A, the user interface in this BLS mode is very spartan. A user is expected in such a mode not to have substantial training, and thus not to need precise control over the defibrillator 102. Thus, the display 104 may provide sufficient direction to the user, perhaps in combination with audible instructions. Also, in this example, the user is not even shown an option for another mode to which to turn the defibrillator 102.

In FIG. 1B, the user has rotated the knob 116 counterclockwise past the "OFF" position, to a heretofore hidden "PACER" position, which may be part of a manual ALS mode for the defibrillator 102. A user who would want to be able to use an ALS mode and would be capable of using such a mode may be presumed to have been highly trained and thus to have been very familiar with the defibrillator 102 and know that the mode is available (though the mode could be indicated on the defibrillator 102 also).

A number of changes can be seen to have occurred in response to the user changing the mode to the ALS mode. For example, a display area above the knob 116 appeared blank when the defibrillator 102 was in BLS mode. Now, however, with the defibrillator 102 in ALS mode, the display area has a number of labels that are visible on it, because, when the user switched the knob 116 to ALS mode, a microprocessor and related circuitry in the device enabled a number of features that are relevant to a highly-trained rescuer, but are not relevant to a less trained rescuer. For example, the display area may show information, including in user-selectable areas, for parameters relating to the level of energy applied to the defibrillator 102 electrodes, and relating to reading of, and control of, ECG-related functions.

Also, a pacer cover 124 that previously covered two adjustment knobs 134, 136 in the lower corner of the defibrillator 102 has pivoted downward and below the defibrillator 102 housing so as to expose the knobs 134, 136. Knob 134 controls the power output of electrodes attached to the defibrillator 102 when they provide a pacing output. Knob 136, when pacing is selected, sets the rate (pulses per minute) at which the pacemaker will operate. The selected pace rate setting is then indicated on the display 104.

The defibrillator 102 may also be provided with additional components that are not visible in these views of the front of the defibrillator. For example, packaged electrodes and associated feedback mechanisms (e.g., a accelerometer-based displacement measurement system) may be attached physically to the side of the defibrillator 102 and may be pre-attached electrically to the defibrillator 102 so as to permit faster deployment of the defibrillator 102 in an emergency situation. Also, a strip chart recorder may be included inside the housing for the defibrillator 102, as may electronic recording mechanisms and components for transferring the electronic data, such as a USB port, WiFi wireless interface, and the like.

Figure 2:
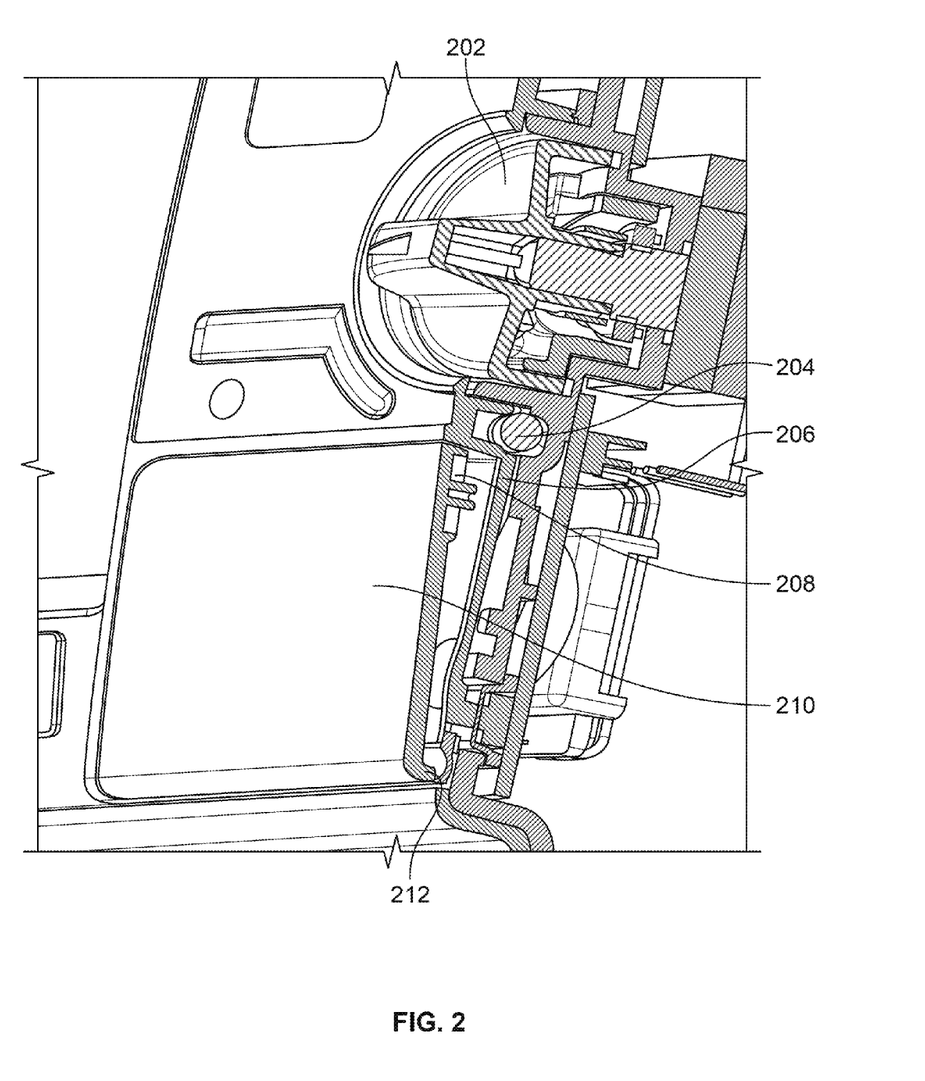
FIG. 2 shows a view in partial section of a door latching and unlatching mechanism for an external defibrillator.

FIG. 2 shows a view in partial section of a door latching and unlatching mechanism for an external defibrillator. The mechanism may be provided on a defibrillator such as in the door 124 in the lower right corner of the front surface of defibrillator 102 in FIGS. 1A and 1B. In general, the door and its associated hardware are arranged so that the door pops open and stays open when the corresponding defibrillator is in a pacing mode which may be part of an ALS, or manual, mode for defibrillation, which is designed for use by very experienced caregivers (e.g., code teams and EMTs).

At the top of the figure is shown a mode selection knob 202. The knob 202 is mounted in a rotatable fashion in the housing for the defibrillator. The knob 202 has a spine across its front-facing edge that a user of the defibrillator may grasp, and that also is printed or embossed with an arrow or other indicator to show a user the direction that the knob 202 is currently pointing. The knob 202 may be provided with stops and blocks in familiar manners so that it "clicks in" to particular positions that correspond to certain modes printed on the front of the defibrillator housing, and so that it cannot move into areas beyond those modes. Also, the knob may be part of a switch having multiple active contact areas, where each contact area corresponds to a particular mode of operation for the defibrillator that corresponds to the position of the knob 202. The contact areas may close circuits or otherwise provide signaling to a central microprocessor that is tasked with coordinating the operation of the defibrillator. For example, the microprocessor may cause certain lights, like those discussed above, to become energized when the defibrillator is in an ALS mode, so that a user can see new features that were previously invisible to the user. The microprocessor may also change the procedures that are followed with the defibrillator, and may change the information that is shown on an electronic display for the defibrillator.

A door 210 on the defibrillator pivots on a hinge 212 that is located at the bottom of the defibrillator. When the door 210 is pivoted to its full-up position, it covers an area on the face of the defibrillator housing, where adjustment knobs or other user-manipulable items may be located. Such items may be applicable only when the device is in a second mode, such as a manual or ALS mode, so that it may be best to hide them from less-experienced users when the defibrillator is in an automatic or BLS mode. In other embodiments, the door 210 may be a sliding door that moves laterally to open a compartment to a user of the defibrillator. The door may also pivot along an arc, such that, as the door opens, the entire door slides underneath the defibrillator, with the pivot point sliding down and backward. Various known mechanisms, such as four-bar and six-bar mechanisms, may be employed to provide an appropriate travel path for the door 210.

A magnet 208, which may be in the form of a disc magnet, may be mounted at an edge of the door that is opposite the edge where the hinge 212 is located. The magnet 208 may thus be used to create a moment about the hinge to cause the door 210 to open or shut, or to stay shut once it is shut. The magnet 208 may be molded into the plastic that makes up the door 210, or may be adhered in a recess in the door 210. The magnet 208 may also be attached to or mounted in the door 210 in various other appropriate manners.

A separate magnet 204 is mounted in a face frame 206 of the defibrillator. The magnet 204 is in close proximity to the magnet 208 when the door is closed, so that magnetic attraction between the two magnets acts to keep the door closed. The magnets 204, 208 are permanent magnets so that they can hold the door 210 closed even in the absence of electrical power being supplied to the medical device, though they could also be implemented as electro-magnets in appropriate circumstances. The magnet 204 is shown in this example as being a spherical magnet and is held loosely between the face frame 206 and another frame of the defibrillator. In this manner, the magnet 204 can rotate, as necessary, as it is held in place.

Also, both of the magnets 204 and 208 may be sealed so that dirt or other materials around the defibrillator cannot get lodged around or behind them. In this manner, the door closing and opening mechanism described here can be implemented more conveniently, in that a user of the defibrillator need not worry about normal waste that is around an emergency medical environment finding its way into the mechanisms.

Figure 3A:
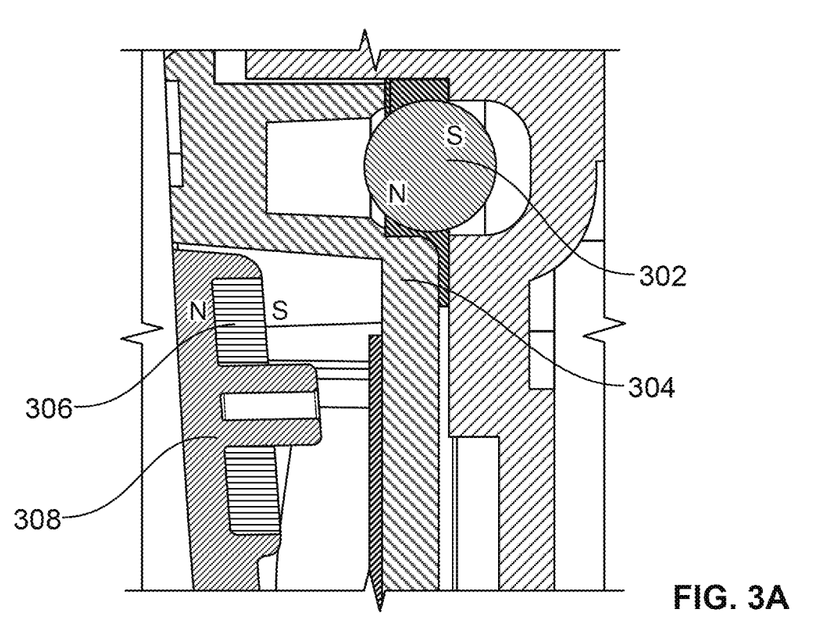
FIGS. 3A and 3B show a cross-sectional close-up views of a door latching mechanism.

FIG. 3A shows a cross-sectional close-up view of a door latching mechanism. The mechanism may be the same as the mechanism shown in FIG. 2, and is shown to include a door 308 in which is mounted a disc magnet 306. In turn, a spherical magnet 302 is mounted between a face frame 304 of a defibrillator and another opposed frame of the defibrillator. The North and South poles of each magnet are shown here, and one can see the relative attraction between the south pole of magnet 306 and the north pole of magnet 302. The magnets may be selected and sized so that the force of attraction between them in this position is sufficient to hold the door 308 closed under typical operation of the defibrillator.

In certain embodiments, the door 308 may be provided with a spring hinge, which may, for example, operate to keep the door 308 opened. (Gravity may also operate to keep the door open when the hinge is at the bottom of the door.) In such a situation, the magnets 302, 306 may be selected, sized, and positioned such that their normal magnetic attraction is greater, when the defibrillator is in a first mode, that the sum of the forces (e.g., spring and gravity) working to open the door.

Figure 3B:
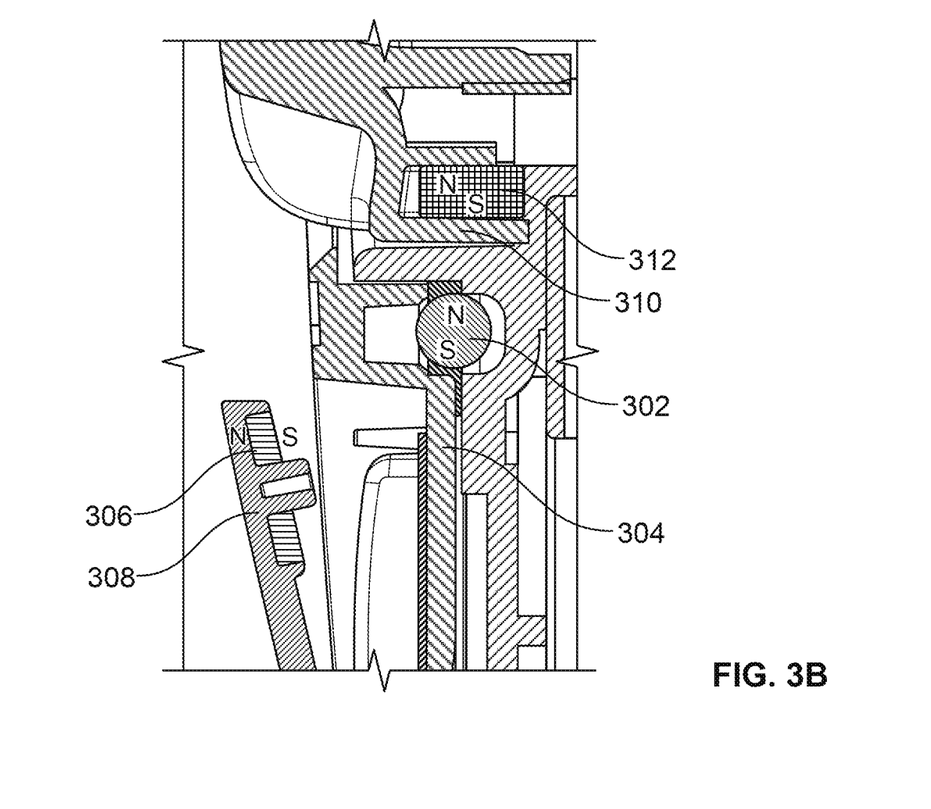

FIG. 3B shows a cross-sectional view of the door latching mechanisms of FIG. 3A, but with a knob rotated so as to place the defibrillator that corresponds to the latching system in a second operational mode. In this example, the view has been expanded out somewhat from that shown in FIG. 3A, so that a bottom portion of a rotating knob 310 is shown in the top of the figure. The knob 310 may be a relatively large physical object on the face of the defibrillator that a user may grasp in order to turn the defibrillator on and off, and to set the operational mode for the defibrillator. The knob may be the largest selectable physical object on the front of the defibrillator in order to emphasize its importance in setting the basic mode for the use of the defibrillator.

As shown in the figure, a magnet 312 is mounted in the knob 310, such as in the form of an arc around part of a peripheral edge of the knob 310. When the knob 310 was rotated to place the defibrillator in BLS mode, the magnet 312 may have been pointing to the side of the knob, which would have placed it out of the general area of magnet 302. However, in placing the defibrillator into ALS mode, and more specifically into a Pacer mode of ALS mode, the knob 310 may have been rotated so that the side of the knob 310 in which the magnet 312 is mounted, is moved close to the magnet 302, so that the magnetic fields of the two magnets 302 and 312 interfere with each other. Such interference is shown in FIG. 3B to have reversed the polarity of the spherical magnet 302, as a result of the magnetic field of magnet 312 overwhelming magnet 302. Such a change causes the magnet 302 to no longer attract magnet 306, and to in fact repel magnet 306, which is shown to have caused the door 308 to be kicked open and away from the defibrillator housing at the door's free edge.

Figure 4:
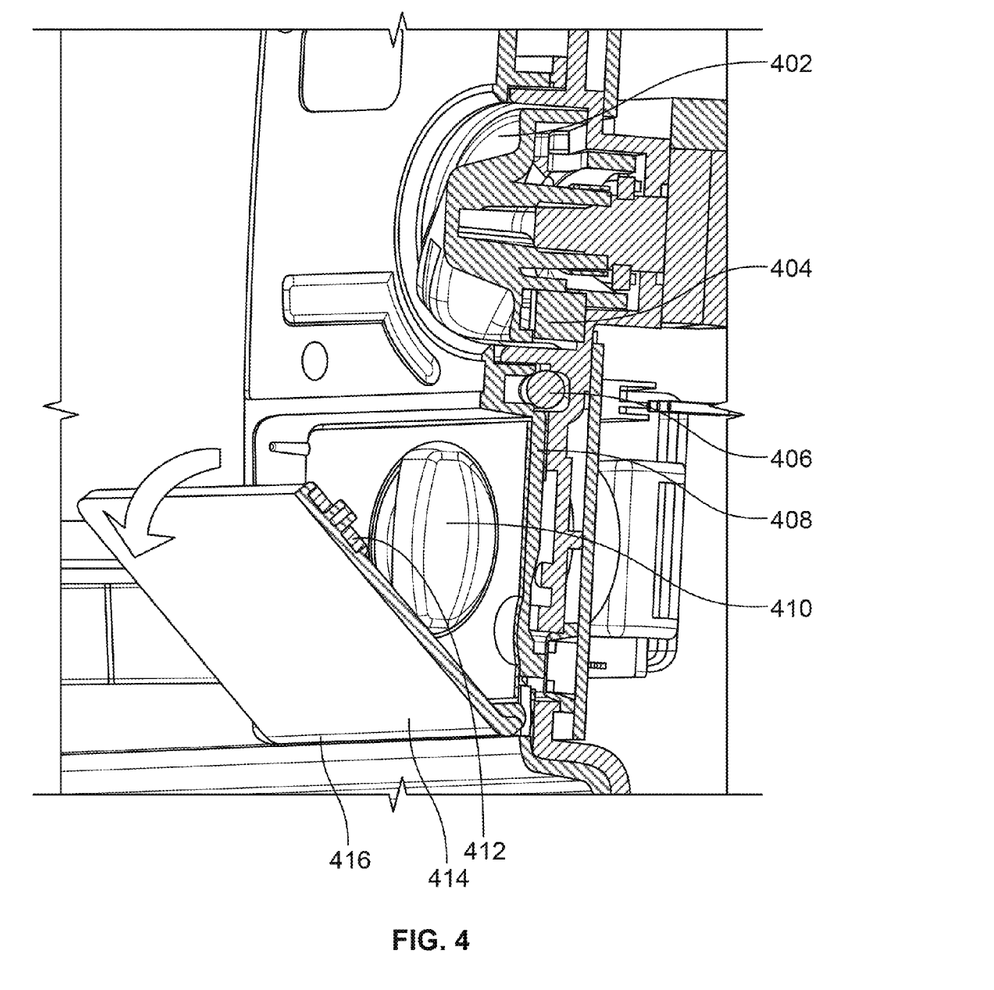
FIG. 4 shows a view in partial section of a defibrillator with its door partially ejected.

FIG. 4 shows a view in partial section of a defibrillator with its door partially ejected, which may be the result of the operation depicted in FIG. 3B. In this example, a rotatable mode selection knob 402 is shown with a magnet 404 mounted near its peripheral edge, in a manner that the magnet 404 traverses an arc as the knob 402 is rotated by a user to change modes on the defibrillator. A spherical magnet 406 is shown mounted in the housing so that the spherical magnet 406 is proximate to the magnet 404 when the knob 402 is in some positions, but not in others. In the depicted example, the knob 402 has been rotated counterclockwise so that the magnet 404 is at the bottom of the knob 402, and is at its closest possible position relative to the spherical magnet 406.

A door 414 mounted to the housing of the defibrillator via a hinge 416 is shown moving downward about the hinged pivot point because a magnet 412 in the door 414 has been pushed away under magnetic force from the spherical magnet 406. An adjustment knob 410 is thus exposed on the front of the housing, and it and the spherical magnet are surrounded by a front frame 408 for the housing. Thus, by rotating the knob 402 counterclockwise, a user of the defibrillator has caused the door 414 to be opened automatically in coordination with switching the defibrillator from one mode to another mode that is relevant to (and can be controlled by) the knob 410. The user thus need not have been distracted from the many other important activities that would be occurring during an emergency response that required deployment of the defibrillator.

Using this structure, the door also cannot be accidentally closed while the defibrillator knob 402 stays in its depicted position. That is because the magnets 404 and 406 are still located in positions from which they will expel the magnet 412. Thus, efforts to close the door manually will be met with the door being automatically re-opened again, until the user moves the knob 402 back to a different position, such as an off position.

In another embodiment, the door 414 could be provided as a sliding door, rather than a rotating door, that has one or more magnets attached to it. The knob 402 could then be attached to a rack-and-pinion type of mechanism that would slide a second magnet laterally above the door as the knob is turned. The second magnet may then interact with the magnet or magnets in the door to "kick" the door in one direction or another based on the position of the knob 402. In particular, the knob 402 could have gear teeth formed about its outer periphery, and a plastic strip may be located horizontally below the knob 402, may have teeth formed in its top surface, and may be located so that those teeth mesh with the teeth of the knob 402 at the bottom-most part of the knob 402 periphery. Rotation of the knob 402 may thus cause the strip to translate laterally back and forth. Likewise, the door 414 may be held in slots so that it can move smoothly laterally below the plastic strip, and may have a magnet at each end. The relative motion of the strip when the knob 402 is turned may then cause magnets attached to the strip to slide laterally and to thus move into or out of magnetic contact with the magnets in the door. Such magnetic contact may create lateral forces in the door 414, so that the door 414 slides to the right or the left to expose or cover certain items as necessary.

Figure 5:
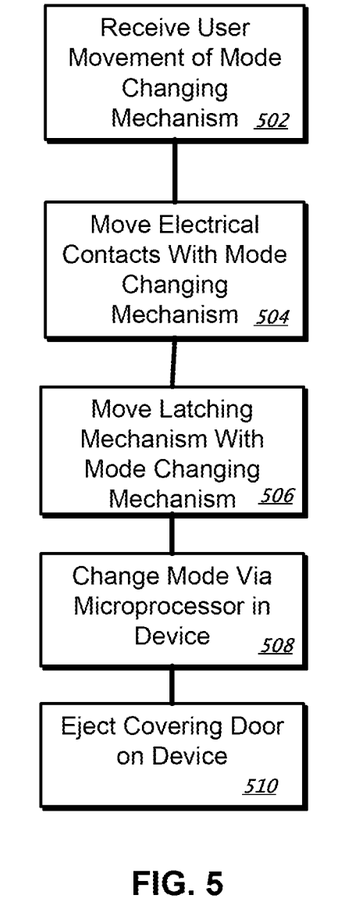
FIG. 5 is a flow chart of a process for unlatching a door of a medical device when transitioned modes with the device.

FIG. 5 is a flow chart of a process for unlatching a door of a medical device when transitioned modes with the device. In general, the process involves mechanical actions that may accompany electronic actions that occur when a user of a medical device, such as a defibrillator, switches the device from a first operational mode, to a second operational mode.

The process begins at box 502, where a medical device receives a user's movement of a mode changing mechanism on the device. The movement actuates a mechanism on the device such as a rotating knob or a slider, so as to cause substantial motion in the mechanism. At box 504, electrical contacts that are associated with the mechanism are moved with the mode changing mechanism. For example, contacts on a shaft of a rotating switch or at a base of a rotating switch may be moved relative to each other, so that the switch senses and registers the movement from the user. The change in relationship of the contacts may then be reported to a microprocessor or other appropriate mechanism operating on the device, so that the device can begin to change modes electronically, e.g., by accepting new inputs that were previously not accepted by the device, and by providing displays and functionality that were not previously provided by the device.

At box 506, a latching mechanism is moved along with the mode changing mechanism. In the examples discussed above, such movement may involve moving a magnet that is attached to move in unison with a knob or other similar mode-changing device. The movement of the magnet may be arranged so that the magnet comes in magnetic range of one or more other magnets, and overcomes a magnetic attraction that previously held a cover, or door, in place when the mode changing mechanism was in its original position. The overcoming of the force may cause the door to kick open, thus revealing additional features of the device that a user should consider in the second mode, but not in the first mode. The position of the magnet may stay the same as long as the mode changing mechanism (e.g., the knob) does not move again, so that the magnet may keep the door from closing throughout such a period.

At box 508, the mode of the device is changed by using a microprocessor in the device, as discussed above. For example, the microprocessor may load instructions from memory that relate to functions to be performed in the second mode, and may begin executing such instructions. The instructions may, for example, provide for the device to begin accepting input from the structures that were previously hidden behind the door that has since been opened. In coordination with such change of the electronic mode of the device, the door may be ejected from the device at box 510, which may be an inherent result of the operations that occurred in box 508. Generally, the changing of the electronic mode and the ejecting of the door, or cover, happen simultaneously, though the timing can be changed somewhat by moving the magnet in the knob, for example, or by providing delays in the software that is executed by the microprocessor. In this context of this document, simultaneity of corresponding actions may be judged against the perception of the user in being presented with the additional items when the user is provided with functionality in the device that responds to inputs to those items (i.e., so that complete simultaneity is not required). In any event, even if the mode change is not simultaneous with the reveal of the extra items, the two actions are automatically coordinated for a user of the device.

Figure 6:
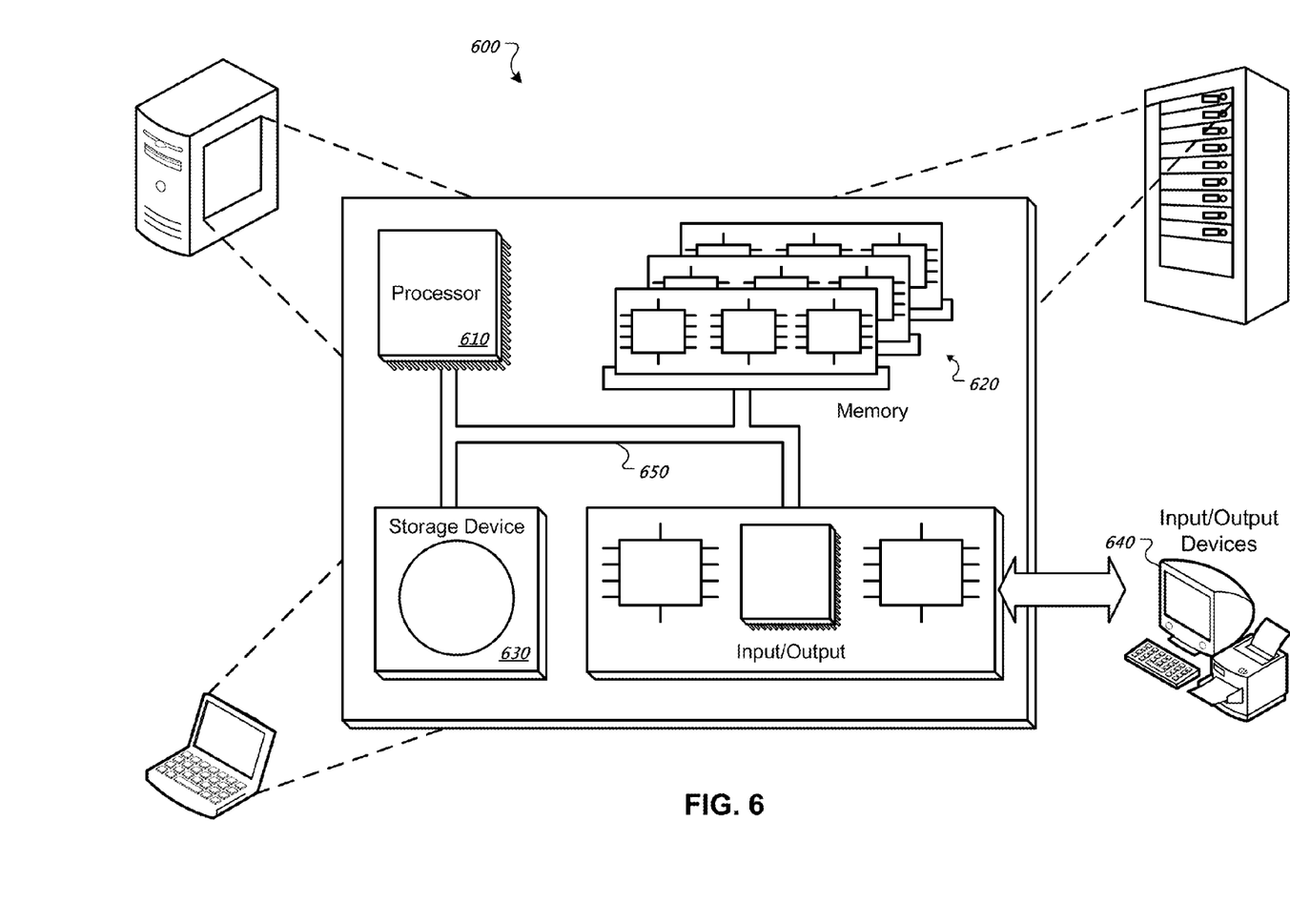
FIG. 6 is a schematic diagram of a general computing system that can be employed to operate a medical device in manners like those discussed here.

FIG. 6 is a schematic diagram of a computer system 600. The system 600 can be used for the operations described in association with any of the computer-implement methods described previously, according to one implementation, such as in changing the electronic mode of a medical device and presenting information on a display screen of an electronic device. The system 600 may take a variety of general forms, as shown, though its preferred form here is as a portable medical device. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them.

The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to a multi-magnet latching mechanism, though other mechanisms may be used that employ the same features as described above. Also, mechanisms other than pivoting doors may be secured and released in similar manners, such as sliding doors and other such structures, as appropriate. Accordingly, other embodiments are within the scope of the following claims.

What is claimed is:

1. A multi-mode electronic medical device, comprising:
a device housing;
a panel mounted to a front side of the device housing, wherein the panel has an open position and a closed position;
a first magnet mounted to the panel; and
a second magnet mounted to an off-center portion of a user-movable mechanism that comprises a rotary switch and is part of the device whose movement from a first position to a second position changes the device from a first mode to a second mode and also moves the second magnet relative to the first magnet so as to automatically move the panel from a closed position to an open position when the device changes from the first mode to the second mode,
wherein the user-movable mechanism is connected to an electric switch and operable to cause the electric switch to change the device from the first mode to the second mode using a same user-provided motion that moves the second magnet from the first position to the second position, and
wherein a third magnet is mounted in an off-center portion of the user-movable mechanism and the first magnet is mounted to the panel away from a hinge for the panel so that magnetic force applied to the first magnet exerts a moment on the panel about the hinge, and magnetic interaction with the first magnet acts to keep the panel closed or to open the panel.

2. The medical device of claim 1, wherein the third magnet is positioned between the first and second magnets when the device is in a second mode so that the second magnet causes the third magnet to rotate such that third magnet repels the first magnet.

3. The medical device of claim 1, further comprising one or more user-manipulable devices located in an area that is hidden by the panel when the device is in the first mode.

4. The medical device of claim 3, further comprising a plurality of visual indicators that are hidden from a user of the device when the device is in the first mode, and are back-lit to be visible by the user when the device is in the second mode.

5. The medical device of claim 1, wherein the second magnet comprises a spherical magnet that is mounted so as to be free to rotate in the device.

6. The medical device of claim 1, wherein the first mode is an advanced life support mode and the second mode is a basic life support mode for a defibrillator.

7. The medical device of claim 1, wherein the panel includes a hinge along a first edge of the panel, and the first magnet is mounted to the panel along a second edge that is opposite the first edge.

8. The medical device of claim 1, wherein the third magnet is positioned to be located between the first magnet and the second magnet when the device is in the second mode.

9. The medical device of claim 8, wherein the third magnet is a rotatable spherical magnet that is arranged to rotate relative to the second magnet when the second magnet is brought in close proximity to the third magnet.

10. The medical device of claim 1, wherein the user-movable mechanism comprises a rotatable user-manipulable knob, and the third magnet is mounted in an edge of the knob.

11. The medical device of claim 1, further comprising a plurality of visual indicators that are hidden from a user of the device when the device is in the first mode, and are back-lit to be visible by the user when the device is in the second mode.

12. The medical device of claim 1, further comprising an electronic display connected to a processor programmed to display a first set of instructions when the device is in the first mode, and a different, second set of instructions when the device is in the second mode.

13. The medical device of claim 12, wherein the processor is programmed to provide audible instructions to a user of the device in coordination with instructions provided on the electronic display, and wherein the audible instructions differ in the first mode compared to the second mode.

* * * * *